United States Patent [19]

Nakamura

[11] 4,200,629
[45] Apr. 29, 1980

[54] ANTI-FUNGAL SUBSTANCE AND PREPARING METHOD THEREOF

[76] Inventor: Junichi Nakamura, Minamiichijonishi-13-chome, Chuo-ku, Sapporo-shi, Japan

[21] Appl. No.: 862,036

[22] Filed: Dec. 19, 1977

Related U.S. Application Data

[63] Continuation of Ser. No. 635,310, Nov. 26, 1975, abandoned.

[51] Int. Cl.$^2$ .................. A01N 9/08; A61K 35/78
[52] U.S. Cl. ............................................. 424/195
[58] Field of Search ............... 260/236 R; 424/195

[56] References Cited

U.S. PATENT DOCUMENTS

| | | | |
|---|---|---|---|
| 2,974,144 | 3/1961 | Klohs et al. | 424/195 |
| 3,541,105 | 11/1970 | Melendez | 260/236 R |
| 3,870,727 | 3/1975 | Powell et al. | 260/236 R |
| 3,879,547 | 4/1975 | Thuillier | 424/195 |

FOREIGN PATENT DOCUMENTS 45-22355  7/1970  Japan .
45-38350 12/1970  Japan ...................................... 424/195

OTHER PUBLICATIONS

Henry, "The Plant Alkaloids", 4th Ed. (1949), published by The Blakiston Co., Phila. Pa., pp. 328-338, 344-345.
Tomita et al., Yakugaku Zasshi, vol. 78, pp. 1444-1447, (1958).
Chemical Abstracts, vol. 47:8175b.
Remington's Pharmaceutical Sciences, 13th Ed., (1965), Mack Publishing Co., pp. 820-823.
Dictionary of the Active Principles of Plants, (1894), Bailliere, Tendall & Cox, London, pp. 20 and 21.

*Primary Examiner*—Donald B. Moyer
*Attorney, Agent, or Firm*—Armstrong, Nikaido, Marmelstein & Kubovcik

[57] ABSTRACT

Berberine type alkaloid is extracted from plant tissue containing the alkaloid with ethanol and contacted with phosphate. The obtained product has a high activity for inhibiting the growth of true fungi such as Blastomyces, Candida, Aspergillus and Trichophyton, and is used for curing human and animal diseases caused by the fungi.

21 Claims, 5 Drawing Figures

ANTI-FUNGAL SUBSTANCE AND PREPARING METHOD THEREOF

This is a continuation, of application Ser. No. 635,310, filed Nov. 26, 1975 now abandoned.

BACKGROUND OF THE INVENTION

This invention relates to true fungi-controlling agents and to a process for preparing the same. More particularly, the invention pertains to true fungi-controlling agents obtained from plants containing berberine type alkaloids and to a process for obtaining the same.

The berberine type alkaloids referred to herein are berberine, coptisine, worenine, palmatine and others which are common in skeletal structure of the formula,

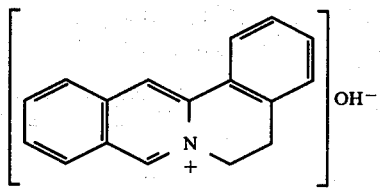

Even until recently, there have not yet been found any effective and accurate processes for the therapy of fungous diseases derived from pathogenic fungi such as Blastomyces, Candida, Cryptococcus, Coccidiodes, Epidermophyton, Histoplasma, Microsporum and Trichophyton. While polyene type antibiotics such as Amphotericin B, Trichomycin and Nystatin are administered at present for the therapy of said diseases, these antibiotics have such drawbacks as being toxic and uneven in antifungal activity, and cannot display effective and accurate therapeutic effects.

An object of the present invention is to provide true fungi-controlling substances which are high in antifungal activity.

Another object of the present invention is to provide a process for producing the said true fungi-controlling substances.

SUMMARY OF THE INVENTION

According to the present invention there are provided a process for preparing a true fungi-controlling substance comprising subjecting berberine type alkaloid-containing plant tissues free from fatty or resinous materials to extracting treatment with a polar solvent, contacting the extract with an aqueous caustic alkali dihydrogenphosphate solution during or after the extraction at a temperature of 35° to 75° C., concentrating the extract solution after the contact with the aqueous caustic alkali dihydrogenphosphate solution to obtain a solution saturated with the extract, mixing the resulting saturated solution with an aqueous dicaustic alkali hydrogenphosphate solution so as to make the pH of the mixture 6.8 to 7.2, evaporating the polar solvent at a temperature of 35° to 75° C., drying the resulting residue under a reduced pressure, extracting the dried matter with a polar solvent, and evaporating the extract solution to dryness; and the product thus obtained.

DESCRIPTION OF PREFERRED EMBODIMENTS

Figure 1:
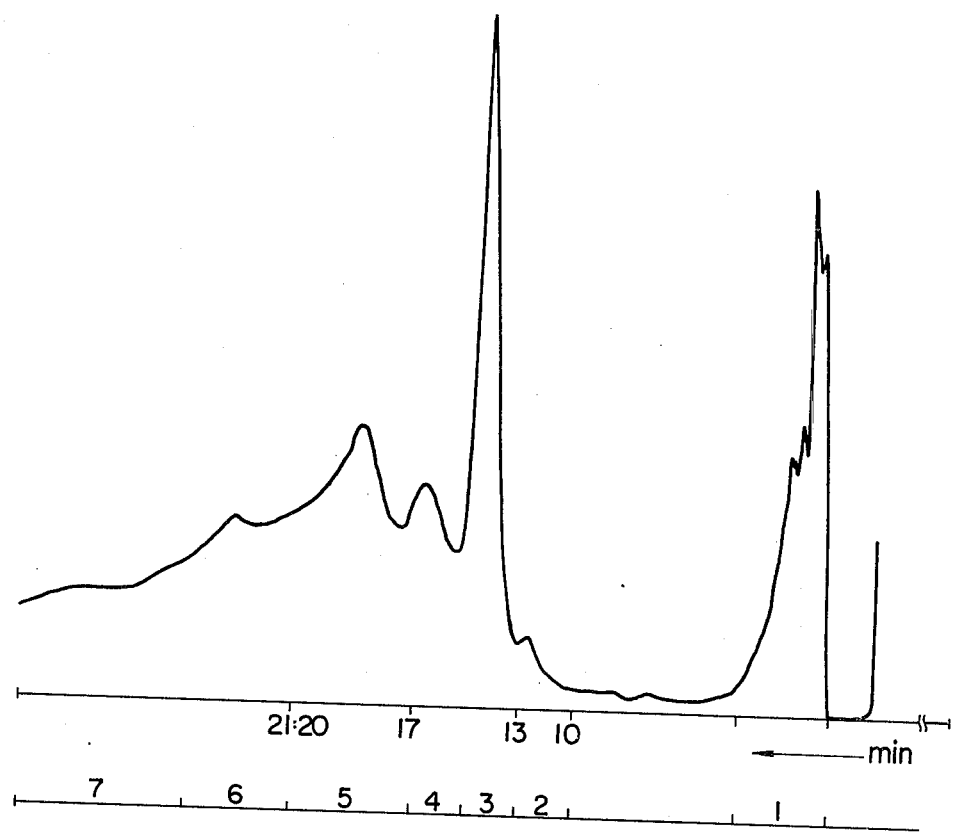

Examples of plants containing berberine type alkaloids are *Phellodendron amurense* Ruprecht, P. amurense Rupr. var. sachalinense, P. amurense Rupr. var. japonicum (Maxin.) Ohwi and P. amurense Rupr. var. Levallei (Dode) Sprague which belong to the family Rutaceae; *Coptis japonica* Makino, *Coptis japenica* Makino var. dissecta Nakoi, *Coptis trifolia salisbuty*, *Exanphorrhiza* and *Xanphorrhiza simplicissima* which belong to the family Ranunculsceae; *Berberis thunberzii*, *Berberis sieboldi*, *Berberis amurensis* and *Nandina domestica* which belong to the family Berberidaceae; and *Costinum fenestratum* and *Columbo radix* which belong to the family Menispermaceae. These plants contain in their tissues berberine type alkaloids such as berberine, palmatine, coptesine, worenine and the like, in the form of hydroxide.

Berberine type alkaloid-containing tissues of these plants, e.g. bark from which cork layers have been moved, of *Phellodendron amurense* Ruprecht belonging to the family Rutaceae, subterranean stems of Xanphorrhiza belonging to the family Ranunculsceae, leaves, stems and roots of *Berberis thunberzii* belonging to the family Berberidaceae, stem of *Costinum fenestratum* belonging to the family Menispermaceae, and leaves and stems of coptis Rhizoma can be used as startng materials. Further, dry powders of tissues of the above-mentioned plants are commercially available as crude drugs under the names of Phellodendron powder, Coptis powder, etc., so that the use of such crude drugs is preferable.

It is preferable that the berberine type alkaloid-containing starting materials are less in content of resinous substances as far as possible. Accordingly, the starting materials are preferably treated previously with a solvent to remove fatty, resinous or tarry substances contained therein. That is, the starting materials, i.e. the aforesaid plant tissues or crude drugs are treated with a non-polar solvent such as ether, petroleum ether, petroleum benzine, benzene, toluene or xylene to remove components soluble in said solvent.

After dried, the residue formed by the extraction with the non-polar solvent is further subjected to extraction with a proper amount such as about 2 to 3 times the volume of a polar solvent such as methanol, ethanol, acetone, acetone alcohol or the like. The extraction is carried out several times preferably at a temperature of 35° to 75° C. until the final extract solution becomes substantially colorless. The extract solution is filtered and added with about ⅛-1/12 volume of 0.5-1.5 M aqueous caustic alkali dihydrogenphosphate solution. The mixture is heated at 35°-75° C. and subjected to evaporation of the polar solvent at that temperature under reduced pressure to obtain a solution saturated with the extract.

The extraction of the dried residue may be carried out by use of a mixture of the polar solvent and the aqueous caustic alkali dihydrogenphosphate solution in a mixing ratio of 5-25:1. In this case, extract solution obtained may immediately be subjected to evaporation of the polar solvent without further treatment with the aqueous caustic alkali dihydrogenphosphate, to obtain the solution saturated with the extract.

The thus obtained solution may be subjected to extraction with ether under acidic condition to further remove impurities dissolving in ether, after complete evaporation of the polar solvent.

The pH of the solution saturated with the extract is made 6.8-7.2 by the use of a solution of dicaustic alkali hydrogenphosphate such as dipotassium or disodiam hydrogenphosphate or phosphoric acid and caustic alkali. The color of the mixture becomes pale yellow brown.

The mixture which is a clear solution is subjected to evaporation under reduced pressure at a temperature of 80° C. or less to obtain a concentrated solution containing desired substances, which may be dried under reduced pressure or by freeze drying.

The concentrated solution containing desired substances may be used as a true fungi-controlling agent, and administered to human or animal after dilution with a proper amount of water. However, it may be further purified by repeating the extraction treatment of the dried matter with the polar solvents and then evaporating the polar solvent to obtain a further purified product. The purified product which is yellow brown crystalline powder will be referred to herein as NT-72.

NT-72 obtained by the process of the present invention can successfully inhibit the growth of various medical fungi such as ones belonging to the genera Aspergillus, Candida, Trichophyton, etc. When incorporated with a phosphate buffer having a pH of 6.8 to 7.2, NT-72 is further enhanced in antifungal activity and can be stored in an extremely stable state. The NT-72 of the present invention is miscible in any proportion with each of hydrophilic and oleophilic ointment base agents, and shows prominent effect for the therapy of dermatophytosis of human or animal when administered in 0.2–0.5 g amounts onto the skin suffering therefrom.

It can orally be administered to a patient suffering from internal fungi-diseases in a dose of about 0.01 to about 0.05 g/kg/day, and by injection in a dose of about 0.001 to 0.005 g/kg/day. The acute toxicity is so low that when orally administered to mice $LD_{50}$ to NT-72 to 7 g/k which is far less in toxicity than berberine hydrochloride showing $LD_{50}$ 60–70 mg/k.

While it has not been clarified yet from which component of the berberine-containing plant is derived the antifungal activity of NT-72, it is inferred that this product might be such a substance in which some of the berberine type alkaloids have combined in a certain form with phosphoric acid.

NT-72 obtained from Phellodendron melts between 63°–116° C. and is a combination of several components. When subjected to high performance liquid chromatography, it has several peaks revealed in the chromatogram. However, the active effectiveness to the growth inhibition of true fungi is seen in two peak portions, among which one is the most active.

Now referring to the drawings attached, the components of NT-72 will be explained.

FIG. 1 is chromatogram resulting from high performance liquid chromatography, under the condition of a pressure of 30 kg/cm², at ambient temperature, a flow rate of 1.6 ml/min, a chart speed of 0.5 cm/min, column of JASKOPACK $SD-C_2-500$, detector being UV-254 UVIDEC-1.2 FP:4, RI, using the apparatus FLC-350 sold by Nihon Bunko Co.

Reviewing FIG. 1, seven peaks are revealed. Peak 1 shows remaining solvents which are water and alcohol. Peaks 2 to 7 show the components of NT-72.

Each of the components is separated and tested with respect to the activity of growth inhibition of *Aspergillus fumigatus*, *Candida albicans* and *Trichophyton mentagrophytes*, respectively, according to the disk method.

Table 1

| Component separated | Inhibitor circle diameter (mm) | | | | | | |
|---|---|---|---|---|---|---|---|
| | 1 | 2 | 3 | 4 | 5 | 6 | 7 |
| *Aspergillus fumigatus* | (—) | 7.0–7.2 trace | (—) | (—) | 16–17 | trace | (—) |
| *Candida albicans* | (—) | 11.5–12.4 | (—) | (—) | 14–15 | (—) | (—) |
| *Trichophyton mentagrophytes* | (—) | 12.5–13.6 | (—) | (—) | 28–29 | trace | (—) |

Assuming that NT-72 contains an inorganic salt of a berberine type alkaloid as active ingredient, when it is freed from such inorganic acid by reducing with sodium borohydride and the resulting substance extracted with various solvents, the most active component is extracted with butanol. When berberine hydrochloride (Japanese Phamacopeia grade) is treated as above, the butanol extract does not show the activity.

The results are shown in Table 2.

Table 2

| NT-72 | Inhibitory circle diameter (mm) | |
|---|---|---|
| | *Aspergillus fumigatus* | *Candida albicans* |
| Methanol sol. | Complete 10.0 Uncomplete 23.0 | 22.0 |
| Aqueous sol. | 18.0 | 30.0 |
| Berberine . HCl | | |
| Methanol sol. | (—) | (—) |
| Aqueous sol. | (—) | (—) |

Figure 2:
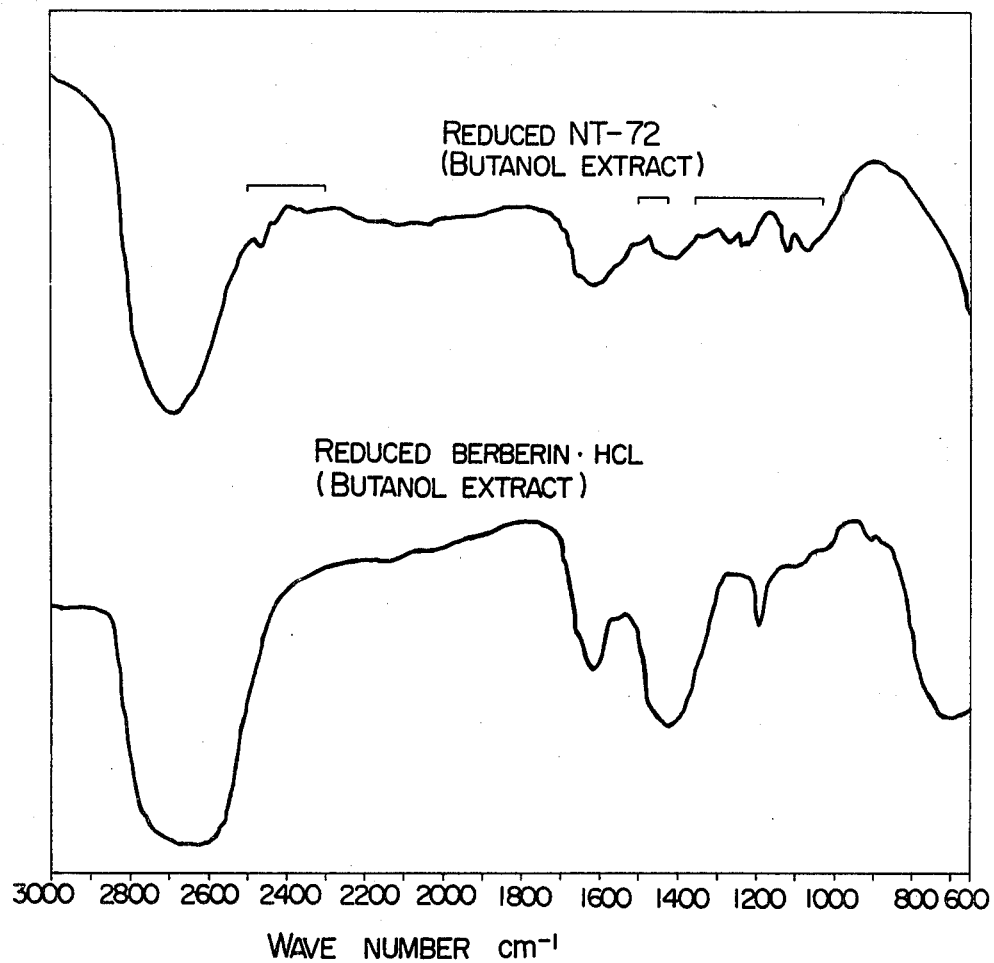

Each of the infra-red adsorption spectra of the butanol extracts is shown in FIG. 2 in which the both substances are different from each other.

Figure 3:
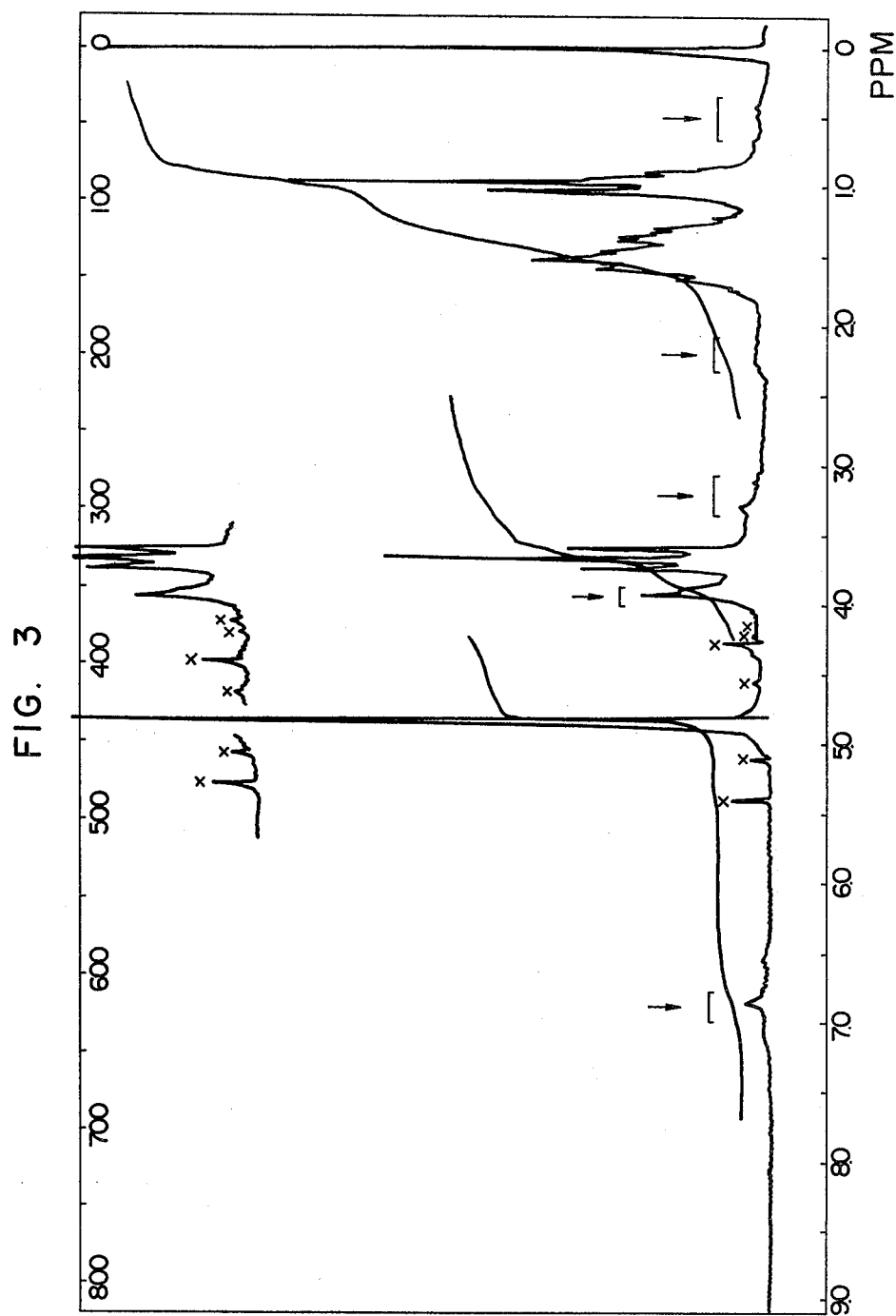
Figure 4:
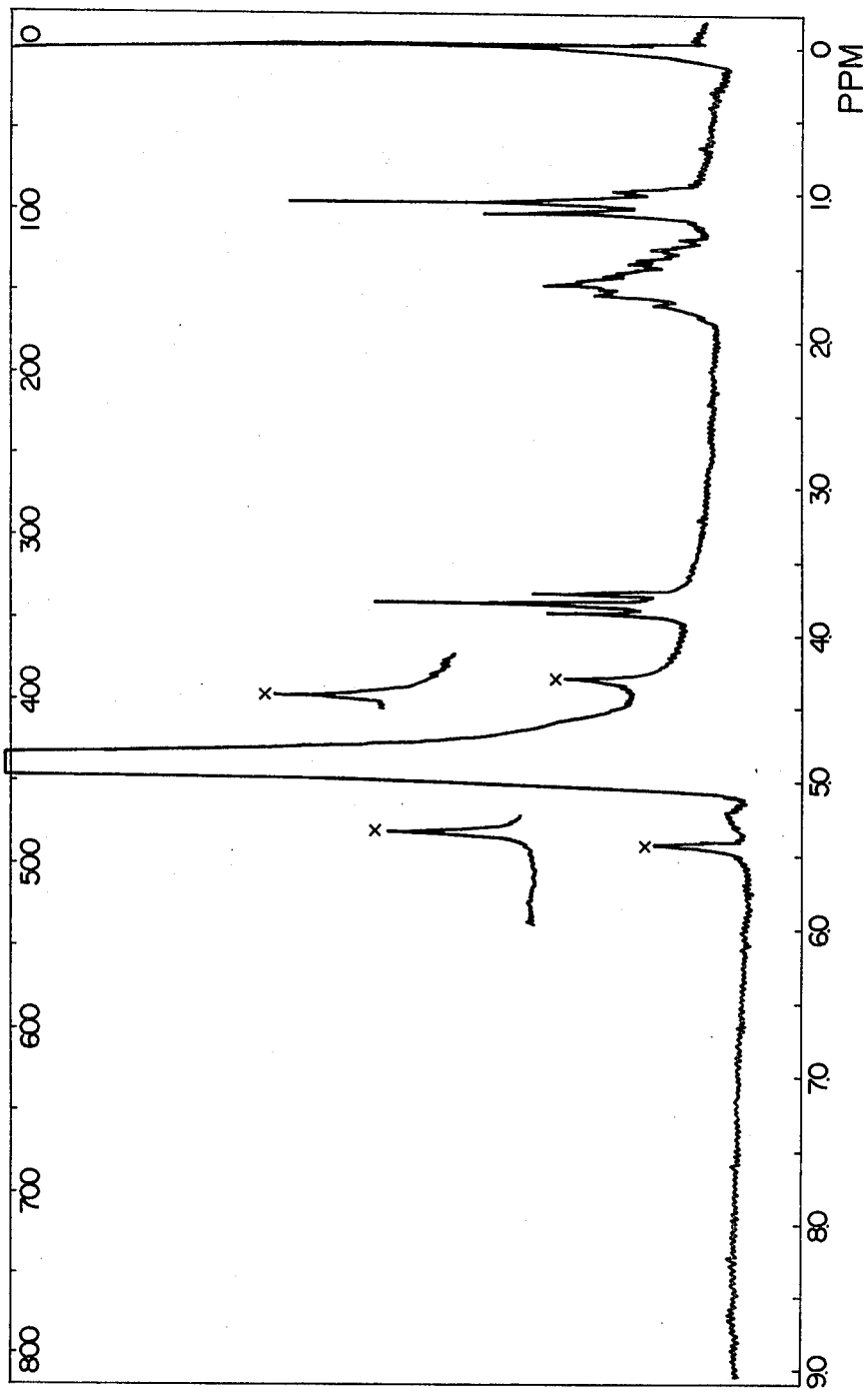

FIGS. 3 and 4 are each N.M.R. spectra of the butanol extracts of the reduced NT-72 and the reduced berberine hydrochloride, respectively, dissolved in heavy water. Common adsorptions are shown by signal X, and adsorptions lacking in berberine are shown by signal ↓.

Figure 5:
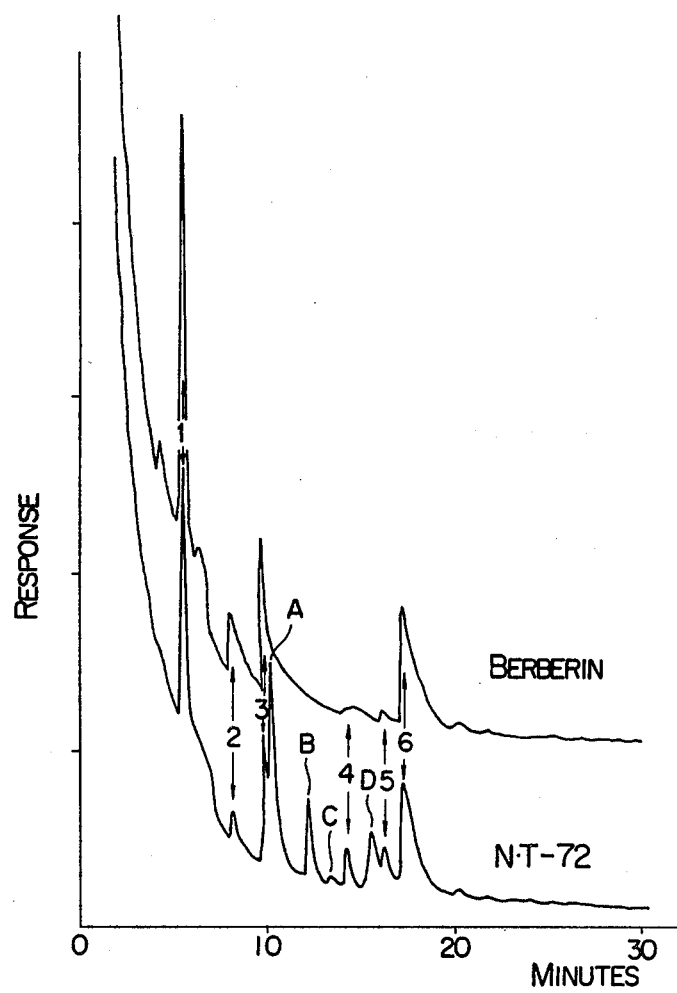

FIG. 5 shows each of the gas chromatograms of the butanol extracts of NT-72 and berberine hydrochloride. From FIG. 5, it will be noted that peaks A, B, C and D are different from each other and peaks 1, 2, 3, 4, 5 and 6 are common. The conditions of the gas chromatography are as follows:
Column:
Gas Chrom P
Silicon GUM SE-30 0.75% FP-2.25 m
Programmed: 40° C.–240° C.
Rate: 4° C./min
Chart speed: 5 mm/min
Apparatus: YANAGIMOTO GCG-550 FP The present invention is illustrated in detail below with reference to examples, test examples and reference examples as well as clinical examples.

EXAMPLE 1

200 Grams of a powder of the bark removed from cork layers of Phellodendron was extracted several times using 500 ml. of ether each time to remove fatty or resinous materials contained therein. To the residue were added 2,000 ml. of ethanol and 25 ml. of a 1 M-aqueous potassium dihydrogenphosphate ($KH_2PO_4$) solution, and the resulting mixture was treated at about 60° C. for 2 to 3 hours, cooled and then filtered. The residue was subjected 3 times to the same extraction operation as above. Thereafter, the filtrates were combined together, and ethanol was removed from the combined filtrate by distillation under reduced pressure at below 60° C. to obtain a solution saturated with extract. The solution was made weakly alkaline (pH 7.2) by addition of a 1 M-aqueous disodium hydrogenphosphate ($Na_2HPO_4$), and then subjected to freeze-drying. After the freeze-drying, the residue was dissolved in 100 ml. of ethanol, and the resulting solution was filtered. Subsequently, the filtrate was evaporated to dryness under reduced pressure at below 60° C. to obtain 20 g. of a yellow brown crystalline powder.

The above-mentioned operation was repeated, except that the ethanol was replaced by each of polar solvents methanol and acetone alcohol, to obtain the same result as above.

EXAMPLE 2

200 Grams of a fine powder of the bark removed from cork layers of Phellodendron was extracted several times using 500 ml. of petroleum ether each time to remove fat and tar contained therein. To the residue were added 2,000 ml. of ethanol and the resulting mixture was heated at about 60° C. for 2 to 3 hours, cooled and then filtered. The residue was subjected 3 times to the same extraction operation as above. Thereafter, the filtrates were combined together, and 25 ml of 1 M-aqueous sodium dihydrogenphosphate was added thereto. The mixture was subjected to distillation to dryness under reduced pressure at 60° C. The residue was dissolved in water, and the resulting solution was shaken 3 times using about ⅓ the amount thereof of ether each time. The formed aqueous layer was recovered, made weakly alkaline (pH 7.2) by addition of a 1 M-aqueous disodium hydrogenphosphate ($Na_2HPO_4$) solution, and then subjected to freeze-drying. After the freeze-drying, the residue was dissolved in 100 ml. of ethanol, and the resulting solution was filtered. Subsequently, the filtrate was evaporated to dryness under reduced pressure at below 60° C. to obtain 20 g. of the same yellow brown crystalline powder as in Example 1.

The above-mentioned operation was repeated, except that the ethanol was replaced by each of polar solvents methanol and acetone, to obtain the same result as above.

REFERENCE EXAMPLE 1

(1) A powder freed from fat and tar, which had been obtained in the same manner as in Example 1 from 200 g. of a Phellodendron powder, was added to 2,000 ml. of an ethanol solution containing 3% of hydrochloric acid. The resulting mixture was allowed to stand overnight at room temperature and then filtered, and the filtrate was concentrated under reduced pressured at below 40° C. The residue was dissolved in water, and the resulting solution was shaken 3 times using about ⅓ the amount thereof of ether each time. The formed aqueous layer was recovered, made neutral to weakly alkaline (pH 7.2) by addition of a 10% aqueous ammonia solution, and then subjected to freeze-drying. After the freeze-drying, the residue was dissolved in 100 ml. of ethanol, and the resulting solution was filtered. Subsequently, the filtrate was evaporated to dryness under reduced pressure at below 60° C. to obtain a yellowish brown powder.

(2) Using 2,000 ml. of ethanol containing 3% of tartaric acid, 200 g. of a Phellodendron powder freed from fat and tar, which had been obtained in the same manner as in Example 1, was treated in the same manner as in (1) to obtain a yellowish brown powder.

(3) Using 2,000 ml. of ethanol containing 3% of acetic acid, 200 g. of a Phellodendron powder freed from fat and tar, which had been obtained in the same manner as in Example 1, was treated in the same manner as in (1) to obtain a yellowish brown powder.

0.02 Gram of each of the yellowish brown powders obtained in the above-mentioned (1) to (3) and the yellow brown crystalline powders obtained in Examples 1 and 2 was orally administered twice a day for two weeks to male mice of 20 to 22 g. in average body weight (1.5 month-old in average). As the result, no dead mice were observed in the groups administered with the yellow brown crystalline powders obtained in Examples 1 and 2 (refer to Table 3).

Table 3

| Extraction process | Number of mice per group | Number of living mice after two weeks | Number of dead mice after two weeks |
|---|---|---|---|
| Reference Example (1) | 10 | 2 | 8 |
| Reference Example (2) | 10 | 7 | 3 |
| Reference Example (3) | 10 | 6 | 4 |
| Example 1 | 10 | 10 | 0 |
| Example 2 | 10 | 10 | 0 |

TEST EXAMPLE 1

Antifungal activity:

0.8 Gram of each of the yellow brown crystalline powders obtained in Examples 1 and 2 was dissolved in 1 ml. of each of a phosphate buffer at pH 6.8 and distilled water. Using 0.01 ml. of the resulting solution, the growth inhibitory effect of each powder against fungi was tested according to the disk method. As the result, an increase in inhibitory effect was observed in the case where the phosphate buffer was used (refer to Table 4).

Table 4

| | Example 1 | | Example 2 | |
|---|---|---|---|---|
| Test fungi | Distilled water | pH 6.8 | Distilled water | pH 6.8 |
| Trichophyton mentagrophytes | 19–21 | 22–23 | 18–21 | 23–24 |
| Candida albicans | 19–21 | 23–24 | 18–20 | 22–24 |
| Aspergillus fumigatus | 19–21 | 23–24 | 19–21 | 23–24 |

[The numberals show inhibitory circle diameters (mm)]

TEST EXAMPLE 2

Each of aqueous solutions of Nystatin, Amphotericin 3 and Byb 5097, and a phosphate buffer solution of the yellow brown crystalline powder produced in Example 1, was applied to an antifungal test disk (diameter 8 mm., weight 0.03 g.) to adsorb thereon 0.005 g. of the active ingredient of each solution, and was observed in inhibitory effect against *Aspergillus fumigatus, Candida albicans, Trichophyton mentagrophytes* and *Cryptococcus neoformans* to obtain such results as shown in Table 5.

Table 5

| | Powder obtained in Example 1 | Amphotericin B | Nystatin | Byb 5097 |
|---|---|---|---|---|
| *Aspergillus fumigatus* | 18 | — (Circular trace) | 12 | 12.5 (Trace 18) |
| *Candida albicans* | 25 | .11 (Trace 14) | 21 | 17 (Trace 22) |
| *Trichophyton mentagrophytes* | 48.5 | 8.5 | 12.5 | 24 |
| *Cryptococcus neoformans* | 11 | — (Circular trace) | 11 | — |

[The numerals show inhibitory circle diameters (mm)]

Each test fungal liquid was mixed with a Sabouraud's agar medium containing 0.1% of Tween 80 to form a multilayered fungal agar film, which was then solidified. Further, each of Amphotericin B, Nystatin and Byb 5097 was not sufficiently soluble in the phosphate buffer solution, but was recognized to have been incorporated therein in an amount necessary for sufficient adsorption on the 8 mm. disk.

EXAMPLE 3

200 Grams of a Coptis powder was extracted 3 times using 500 ml. of ether each time to remove fatty or resinous materials contained therein. The solid residue was dried and then charged with 2,000 ml. of ethanol, and the resulting mixture was allowed to stand at about 60° C. for 2 hours. To the mixture was then added 40 ml. of a 1 M-aqueous potassium dihydrogenphosphate ($KH_2PO_4$) solution, and the mixture was heated at about 60° C., cooled and then filtered. The residue was subjected 3 times to the same extraction operation as above. Thereafter, the filtrates were combined together, and then subjected to reduced pressure distillation at below 60° C. The residue was made weakly alkaline (pH 7.2) by addition of a 1 M-aqueous disodium hydrogenphosphate ($Na_2HPO_4$) solution, further freed completely from ethanol by distillation, and then subjected to freeze-drying. After the freeze-drying, the residue was dissolved in 100 ml. of ethanol, and the resulting solution was filtered. Subsequently, the filtrate was evaporated to dryness under reduced pressure at below 60° C. to obtain 20 g. of a yellow brown crystalline powder.

EXAMPLE 4

200 Grams of a Coptis powder was extracted 3 times using 500 ml. of ether each time to remove fatty or resinous materials contained therein. To the residue were added 2,000 ml. of ethanol and 56 ml. of a 1 M-aqueous dipotassium hydrogenphosphate, and the resulting mixture was digested at about 60° C. for 2 hours, cooled and then filtered. The residue was subjected 3 times to the same extraction operation as above. Thereafter, the filtrates were combined together, and ethanol was removed from the combined filtrate by distillation under reduced pressure at below 60° C. The residue was dissolved in water, and the resulting solution was shaken 3 times using about ⅓ the amount thereof of ether each time. The formed aqueous layer was recovered, made weakly alkaline (pH 7.2) by addition of a 1 M-aqueous disodium hydrogenphosphate ($Na_2HPO_4$) solution, and then subjected to freeze-drying. After the freeze drying, the residue was dissolved in 100 ml. of ethanol, and the resulting solution was filtered. Subsequently, the filtrate was evaporated to dryness under reduced pressure at below 60° C. to obtain 20 g. of the same yellow brown crystalline powder as in Example 3.

The thus obtained powder was dissolved in 100 ml. of a phosphate buffer (comprising 40 ml. of M/15 $KH_2PO_4$ and 60 ml. of M/15 $Na_2HPO_4$) to prepare a stable solution having a pH of 7.0. This solution was stored at 30° C. for 6 months, but no change in antifungal activity was observed.

EXAMPLES 5-10

Example 1 was repeated with the exception that in place of the bark of Phellodendron each of starting materials indicated in Table 6 was used. The yields, antifungal activities and acute toxicities of the products are shown in Table 6.

The antifungal activity was evaluated according to the method described in Test Example 1.

The acute toxicity was evaluated as follows:

Each of the products obtained in Examples were formed into aqueous solutions, which were then diluted with water in such proportions as 65–70 mg/ml, 70–75 mg/ml, 75–80 mg/ml and 80–85 mg/ml, and the resulting dilutions were subjected to acute toxicity test. The test was carried out in such a manner than each test solution was intravenously injected into the tails of 20 mice (male and female) per groups (85 mice were reserved) which were 21 to 24 g. in body weight and 22.6 g. in average body weight, and the survival state of the mice was observed. The results obtained were as set forth in Table 6. The numerals in Table 6 represent survival ratios of the mice; for example 10/10 shows that 10 of the ten mice were survived, and 8.2/10 shows that 8.2 of the ten mice were survived.

Table 6

| | | | Antifungal activity | | | Acute toxicity | | | | |
|---|---|---|---|---|---|---|---|---|---|---|
| Example No. | Starting materal (portion) | Yield (g) | *Aspergillus fumigatus* | *Candida albicans* | *Trichophyton mentagrophytes* | 65–70 mg/ml | 70–75 mg/ml | 75–80 mg/ml | 80–85 mg/ml | 85–90 mg/ml |
| 5 | *Costinum fenestratum* (barks) | 18.19 20–23 | 18–20 | 26–27 | 8.6/10 | 8/10 | 7.6/10 | 6/10 | 5/10 | |
| 6 | *Berberis Thunberzii* (leaves) | 15.5 | 20–22 | 20–23 | 28–30 | 10/10 | 10/10 | 8.2/10 | 6.8/10 | 6/10 |
| 7 | *Berberis Thunberzii* (stems) | 20.2 | 23–24 | 21–23 | 28–32 | 10/10 | 8/10 | 7/10 | 6.2/10 | 6/10 |
| 8 | *Berberis Sieboldi* | 17.0 | 20–23 | 21–22 | 27–28 | 10/10 | 10/10 | 10/10 | 9/10 | 7/10 |

Table 6-continued

| Example No. | Starting material (portion) | Yield (g) | Antifungal activity | | | Acute toxicity | | | | |
|---|---|---|---|---|---|---|---|---|---|---|
| | | | Aspergillus fumigatus | Candida albicans | Trichophyton mentagrophytes | 65–70 mg/ml | 70–75 mg/ml | 75–80 mg/ml | 80–85 mg/ml | 85–90 mg/ml |
| 9 | (trunks) Phellodendron (barks) Berberis Thunberzii (leaves) Each 100 | 17.5 | 18–19 | 18–19 | 24–25 | 9/10 | 7.6/10 | 6.4/10 | 5.2/10 | 5/10 |
| 10 | Phellodendon (barks) Collumbo Radix (fruits) 50:150 | 16.3 | 22–24 | 20–24 | 28–31 | 10/10 | 8/10 | 7.2/10 | 7/10 | 6/10 |

EXAMPLES 11 and 12

Example 1 was repeated with the exception that in place of the bark of Phellodendron each of starting materials indicated in Table 7 was used and that in place of ether petroleum ether was used. The yield, antifungal activities and acute toxicities of the products evaluated as in the previous Examples are shown in Table 7.

Table 7

| Example No. | (Starting material (portion) | Yield (g) | Angifungal activity | | | Acute toxicity | | | | |
|---|---|---|---|---|---|---|---|---|---|---|
| | | | Aspergillus fumigatus | Candida albicans | Trichophyton mentagrophytes | 65–70 mg/ml | 70–75 mg/ml | 75–80 mg/ml | 80–85 mg/ml | 85–90 mg/ml |
| 11 | *Costinum fenestratum* (stems, roots) | 18.2 | 22–24 | 21–23 | 28–30 | 8.7/10 | 8/10 | 7/10 | 5.6/10 | 5/10 |
| 12 | Coptis powder | 15.1 | 20–22 | 15–16 | 20–22 | 9/10 | 8.2/10 | 7/10 | 5.6/10 | 5/10 |

CLINICAL EXAMPLE 1

A solution was prepared so that 0.4 g. of the yellow brown crystalline powdery substance produced in Example 1 was dissolved in 1 ml. of a phosphate buffer. This solution was used as an original liquid (final pH 7.2).

The original liquid was diluted to 50 times, and 30 ml. (0.24 g. in terms of the yellow brown powdery substance) of the dilution was orally administered thrice a day for 1 to 3 weeks to each of such patients as set forth in Table 8 who were suffering also from fungous pneumonia or urinary tract infection to observe the increase or decrease in number of fungi and bacteria in sputum and urine and the variation in concentration of alkaloid in the blood. The results obtained were as shown in Table 8.

As is clear from Table 8, it was recognized that the amounts of fungi and bacteria in the sputum and urine decreased or were made nil with increasing concentration of the product of the invention in the blood, and that the yellow brown powdery substance of the present invention is clinically effective not only against fungi but also becterial infectious diseases derived from *Pseudomonas aeruginosa, Escherichia coli* and *Micrococcus pyogenes*. Further, there were observed therapeutic effects accompanying the alleviation of fever and the decrease or disappearance of chest X-ray shades. The administration of the said drug caused no injury to the functions of liver and kidney nor other side effects.

Table 8

| Name of disease | | Initial value | First week | Second week | Third week | Fourth week |
|---|---|---|---|---|---|---|
| Parkinson (Total stiffness) ♂ 59 years old | Bacterial test | In sputum Candida | (Number of cells) 7,000 —▸ 80 —▸ 55 —▸ 3,000 | | | |
| | | In urine Escherichia | 300 —▸ 400 —▸ 200 —▸ (—) | | | |
| | Concentration in blood Administration period | (2 hrs. after administration) 0.12 (γ/ml) | 8 | 18 | 1.5 | |
| | | | ←14 days→ | | | |
| Fungous meningitis (*Aspergillus* disease) ♀ 41 years old | Bacterial test | In sputum Pseudomanas 2,000 Candida 800 | | | | |
| | | In urine Candida Escherichia | 600 —▸ 40,000 —▸ 500 3,000 —▸ 6,000 —▸ 4,500 | | | |
| | Concentration in blood | (2 hrs. after admnistration) 0.4 (γ/ml) | | | | |

Table 8-continued

| Name of disease | Initial value | | First week | Second week | Third week | Fourth week |
|---|---|---|---|---|---|---|
| | Administration period | | ←7 days→ | | | |
| Spinal damage | Bacterial test | In Sputum Pseudomonas In urine Staphylococcus | 50,000 --- 80,000 140 --- 200 → 400 --- 10 | | | |
| ♂ 27 years old | Concentration in blood | (2 hrs. after administration) + (γ/ml) | | 8.8 | 5 | |
| | Administration period | | ←7 days→ | | | |
| Wrench | | In sputum Pseudomonas In urine | 140,000 --- 140 --- 20 --- (—) | | | |
| ♂ 39 years old | Bacterial test | Pseudomonas Staphylococcus 600 Escherichia | 600 --- 600 --- 1,000 --- 600 400 | | | |
| | Concentration in blood | (2 hrs. after administration) ± (γ/ml) | 2.4 | 2.2 | 25 | |
| | Administration period | | ←21 days→ | | | |
| Rupture of cerebral aneurism | Bacterial test | In sputum Candida In urine Pseudomonas | 160,000 --- 4,000 --- 3,000 --- 70,000 --- 30 60,000 --- 5,000 --- 1,000 --- 60,000 --- 7,000 | | | |
| ♀ 67 years old | | Candida | 200 | | | |
| | Concentration in blood | (3 hrs. afer administration) 0.5 (γ/ml) | 2.2 | 18 | 0.8 | 40 |
| | Administration period | | ←14 days→ | | ←7 days→ | |
| Cerebral thrombosis | Bacterial test | In sputum Candida Escherichia 20,000 In urine | 40,000 --- 40 --- 30,000 --- 3,000 --- (—) 350 | | | |
| ♂ 59 years old | | Escherichia Candida | 8,000 --- (—) | | 460 --- (—) | |
| | Concentration in blood | (3 hrs. after administration) ± (γ/ml) | 8 | 1.8 | 12 | 16 |
| | Administration period | | ←28 days→ | | | |
| Cerebral thrombosis | Bacterial test | In sputum Candida Micrococcus in urine Candida Staphylococcus | 100,000 --- 20 --- 400 --- 200 8,000 --- 8,000 --- 400 400 --- 20 --- (-) --- (— 140 --- (-) --- (—) | | | |
| ♂ 59 years old | | | | | | |
| | Concentration in blood | (3 hrs. after administration ± (γ/ml) | 24 | 16 | 16 | |
| | Administration period | | ←21 days→ | | | |

(Note 1)
Candida: *Candida albicans*
Pseudomonas: *Pseudomonas aeruginosa*
Escherichia: *Escherichia coli*
Staphylococcus: *Staphylococcus aureus*

(Note 2)
The bacterial test was conducted every 7th day. The measurement of concentration in blood was first carried out 2 to 3 hours after administration of the drug, and thereafter effected every 7th day simultaneously with the bacterial test.

(Note 3)
The concentration of alkaloid in blood was determined by two methods; a method using a Wagner reagent, and a method of testing antifungal value of serum against Aspergillus fumigatus (100,000/ml).

What is claimed is:

1. A process for preparing a composition for treating fungous diseases derived from pathogenic fungi comprising the steps of treating plant tissue containing a berberine type alkaloid having the skeletal structure

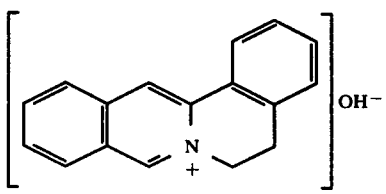

the plant tissue being that of plants selected from the group consisting of *Phellodendron amurense* Ruprecht; *P. amurense* Rupr. var. sachalinense; *P. amurense* Rupr. Var. japonicum (Maxim.) Ohwi; *P. amurense* Rupr. var. Levallei (Dode) Sprague; *Coptis japonica* Makino; *Coptis japonica* Makino var. dissecta Nakoi; *Coptis trifolia salisbuty; Exanphorrhiza; Xanphorrhiza simplicissima;*

*Berberis Thunberzii, Berberis sieboldi; Berberis amurensis; Nandina domestica; Costinum fenestratum, Columbo Radix* and mixtures thereof with a non-polar solvent to prepare plant tissue free from fatty or resinous materials; extracting the plant tissue free from fatty or resinous materials with a polar solvent until a substantially colorless extract solution is obtained; combining the extract solution with an aqueous caustic alkali dihydrogenphosphate solution; heating the resultant mixture at a temperature of 35°–75° C.; concentrating the extract solution by evaporating off the polar organic solvent under reduced pressure; mixture the resulting concentrated solution with an amount of an aqueous dicaustic alkali hydrogenphosphate solution to adjust the pH of the mixture to 6.8–7.2; and drying the mixture under reduced pressure or freeze drying it to obtain a solid product.

2. A process for preparing a composition for treating fungous diseases derived from pathogenic fungi comprising the steps of treating plant tissue containing a berberine type alkaloid having the skeletal structure

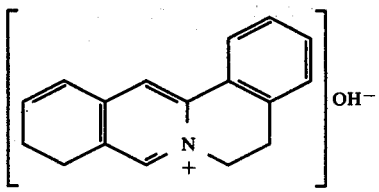

the plant tissue being that of plants selected from the group consisting of *Phellodendron amurense* Ruprecht; *P. amurense* Rupr. var. sachalinense; *P. amurense* Rupr. var. japonicum (Maxim.) Ohwi; *P. amurense* Rupr. var. Levallei (Dode) Sprague; *Coptis japonica* Makino; *Coptis japonica* Makino var. *dissecta Nakoi; Coptis trifolia salisbuty; Exanphorrhiza; Xanphorrhiza simplicissima; Berberis Thunberzii; Berberis sieboldi; Berberis amurensis; Nandina domestica; Costinum fenestratum, Columbo Radix* and mixtures thereof with a non-polar solvent to prepare plant tissue free from fatty or resinous materials; extracting the plant tissue free from fatty or resinous materials with a mixture of a polar organic solvent and an aqueous caustic alkali dihydrogenphosphate solution until a substantially colorless extract solution is obtained; heating the resultant mixture at a temperature of 35°–75° C.; concentrating the extract solution by evaporating off the polar organic solvent under reduced pressure; mixing the resulting concentrated solution with an amount of an aqueous dicaustic alkali hydrogenphosphate solution to adjust the pH of the mixture to 6.8–7.2; and drying the mixture under reduced pressure or freeze drying it to obtain a solid product.

3. The process according to claim 1, wherein the solid product is further extracted with a polar organic solvent and dried to obtain a purified product.

4. The process according to claim 1, wherein the plant tissue is selected from the group consisting of *Phellodendron amurense* Ruprecht; *P. amurense* Rupr. var. sachalinense; *P. amurense* Rupr. var. japonicum (Maxim.) Ohwi; *P. amurense* Rupr. var. Levallei (Dode) Sprague.

5. The process according to claim 1, wherein the plant tissue is a mixture of *Columbo Radix* and *Berberis Thunberzii*.

6. The process according to claim 1, wherein the non-polar solvent is selected from the group consisting of diethyl ether, petroleum ether, petroleum benzine, benzene, toluene and xylene.

7. The process according to claim 1, wherein the polar solvent used in the extraction of the berberine type alkaloid-containing plant tissue free from fatty or resinous materials is methyl alcohol, ethyl alcohol, acetone or acetone alcohol.

8. The process according to claim 1, wherein the extraction is carried out at a temperature of 35°–75° C.

9. The process according to claim 1, wherein the aqueous caustic alkali dihydrogenphosphate solution has a concentration of 0.5 to 1.5 M.

10. The process according to claim 1, wherein the amount of the aqueous caustic alkali dihydrogenphosphate to be contacted with the extract is about ⅛–1/12 time the volume of the polar solvent used in the extracting treatment of the tissue.

11. The process according to claim 1, wherein the concentration of the extract solution is carried out by evaporating the polar solvent at a temperature of 35°–75° C. under reduced pressure.

12. The process according to claim 1, wherein the caustic alkali dihydrogenphosphate is potassium dihydrogenphosphate or sodium dihydrogenphosphate.

13. The process according to claim 1, wherein the dicaustic alkali hydrogenphosphate is dipotassium hydrogenphosphate or disodium hydrogenphosphate.

14. The process according to claim 1, wherein the drying is carried out by freeze-drying.

15. The process according to claim 1, wherein the polar solvent employed in the extraction steps is ethyl alcohol.

16. The process according to claim 1, wherein the berberine type alkaloid is berberine, coptisine, worenine or palmatine.

17. A composition for treating fungous diseases derived from pathogenic fungi and prepared by a process comprising the steps of treating plant tissue containing a berberine type alkaloid having the skeletal structure

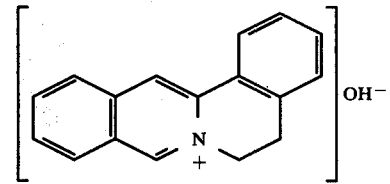

the plant tissue being that of plants selected from the group consisting *Phellodendron amurense* Ruprecht; *P. amurense* Rupr. var. sachalinense; *P. amurense* Rupr. var. japonicum (Maxim.) Ohwi; *P. amurense* Rupr. Var. Levallei (Dode) Sprague; *Coptis japonica* Makino; *Coptis japonica* Makino var. dissecta Nakoi; *Coptis trifolia salisbuty; Exanphorrhiza; Xanphorrhiza simplicissima; Berberis Thunberzii, Berberis sieboldi; Berberis amurensis; Nandina domestica; Costinum fenestratum, Columbo Radix* and mixtures thereof with a non-polar solvent to prepare plant tissue free from fatty or resinous materials; extracting the plant tissue free from fatty or resinous materials with a mixture of a polar organic solvent and an aqueous caustic alkali dihydrogenphosphate solution until a substantially colorless extract solution is obtained; heating the resultant mixture at a temperature of 35°–75° C.; concentrating the extract solution by evaporating off the polar organic solvent under reduced pressure; mixing the resulting concentrated solution with an amount of an aqueous dicaustic alkali hydrogenphosphate solution to adjust the pH of the mixture to 6.8–7.2; and drying the mixture under reduced pressure or freeze drying it to obtain a solid product.

18. The composition of claim 17 in combination with caustic alkali phosphates imparting a buffer solution of pH 6.8–7.2.

19. The composition of claim 17 wherein said pathogenic fungi are Blastomyces, Candida, Cryptococus Coccidiodes, Epidermophyton, Histoplasma, Microsporum or Trichlophyton fungi.

20. A process for preparing a true-fungi controlling composition comprising the steps of extracting a member selected from the group consisting of Phellodendron powder and Coptis powder with a polar organic solvent until a substantially colorless extract solution is obtained; combining the extract solution with an aqueous caustic alkali dihydrogenphosphate solution; heating the resultant mixture at a temperature of 35°–75° C.; concentrating the extract solution by evaporating off the polar organic solvent under reduced pressure; mixing the resulting concentrated solution with an amount of an aqueous dicaustic alkali hydrogenphosphate solution to adjust the pH of the mixture to 6.8–7.2; and drying the mixture under reduced pressure or freeze drying it to obtain a solid product.

21. A process for preparing a true-fungi controlling composition comprising the steps of extracting a member selected from the group consisting of Phellodendron powder and Coptis powder with a mixture of a polar organic solvent and an aqueous caustic alkali dihydrogenphosphate solution until a substantially colorless extract solution is obtained; heating the resultant mixture at a temperature of 35°–75° C.; concentrating the extract solution by evaporating off the polar organic solvent under reduced pressure; mixing the resulting concentrated solution with an amount of an aqueous dicaustic alkali hydrogenphosphate solution to adjust the pH of the mixture to 6.8–7.2; and drying the mixture under reduced pressure or freeze drying it to obtain a solid product.

* * * * *